US012663398B2

(12) United States Patent
Watanabe et al.

(10) Patent No.: US 12,663,398 B2
(45) Date of Patent: Jun. 23, 2026

(54) GAS SENSOR

(71) Applicant: NGK INSULATORS, LTD., Nagoya (JP)

(72) Inventors: Yusuke Watanabe, Nagoya (JP); Yohei Goro, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 273 days.

(21) Appl. No.: 18/489,293

(22) Filed: Oct. 18, 2023

(65) Prior Publication Data

US 2024/0133839 A1    Apr. 25, 2024
US 2024/0230582 A9    Jul. 11, 2024

(30) Foreign Application Priority Data

Oct. 24, 2022    (JP) ................................. 2022-169878

(51) Int. Cl.
| | |
|---|---|
| *G01N 27/409* | (2006.01) |
| *G01N 27/30* | (2006.01) |
| *G01N 27/406* | (2006.01) |
| *G01N 27/41* | (2006.01) |
| *G01N 27/419* | (2006.01) |
| *G01N 33/00* | (2006.01) |

(52) U.S. Cl.
CPC ......... *G01N 27/409* (2013.01); *G01N 27/301* (2013.01); *G01N 27/4067* (2013.01); *G01N 27/41* (2013.01); *G01N 27/419* (2013.01); *G01N 33/0037* (2013.01)

(58) Field of Classification Search
CPC ............... G01N 27/409; G01N 27/301; G01N 27/4067; G01N 27/41; G01N 27/419; G01N 33/0037
See application file for complete search history.

(56) References Cited

U.S. PATENT DOCUMENTS

| | | | | |
|---|---|---|---|---|
| 6,083,370 A | * | 7/2000 | Kato | .................. G01N 27/4065 |
| | | | | 204/425 |
| 6,120,663 A | * | 9/2000 | Kato | .................... G01N 27/419 |
| | | | | 204/425 |

(Continued)

FOREIGN PATENT DOCUMENTS

| | | | |
|---|---|---|---|
| JP | 3340110 | B2 | 11/2002 |
| JP | 2022-091669 | A | 6/2022 |

*Primary Examiner* — Ryan D Walsh
(74) *Attorney, Agent, or Firm* — MATTINGLY & MALUR, PC

(57) ABSTRACT

A gas sensor includes: an element body which is internally provided with a measurement-object gas flow portion; a first pump cell including a first inner electrode disposed in the measurement-object gas flow portion; a second pump cell including a second inner electrode disposed in the measurement-object gas flow portion; a heater; a first impedance measurer configured to measure a first impedance by applying a voltage to the first inner electrode; a second impedance measurer configured to measure a second impedance by applying a voltage to the second inner electrode; and a control apparatus configured to perform a heater control process of controlling the heater so that the first impedance reaches a target value, and a correction process of correcting, based on the second impedance, a second pump current which flows through the second pump cell or a value derived based on the second pump current.

3 Claims, 5 Drawing Sheets

(56)  References Cited

U.S. PATENT DOCUMENTS

| | | | |
|---|---|---|---|
| 6,287,439 B1 * | 9/2001 | Kato | G01N 27/407 |
| | | | 219/209 |
| 6,348,140 B1 | 2/2002 | Matsubara et al. | |
| 6,453,724 B1 * | 9/2002 | Kawase | G01N 27/4067 |
| | | | 73/23.31 |
| 6,547,955 B1 * | 4/2003 | Hada | G01N 27/4067 |
| | | | 204/406 |
| 10,895,553 B2 * | 1/2021 | Mizutani | G01N 27/416 |
| 2002/0050455 A1 * | 5/2002 | Kurokawa | G01N 27/419 |
| | | | 204/431 |
| 2012/0199478 A1 * | 8/2012 | Sasaki | G01N 27/419 |
| | | | 204/406 |
| 2017/0010236 A1 * | 1/2017 | Sakashita | F01N 11/007 |
| 2022/0178869 A1 | 6/2022 | Okamoto et al. | |
| 2023/0194463 A1 * | 6/2023 | Goro | G01N 27/409 |
| | | | 204/424 |
| 2023/0228702 A1 * | 7/2023 | Watanabe | G01N 27/4067 |
| | | | 204/424 |
| 2023/0228703 A1 * | 7/2023 | Watanabe | G01N 27/409 |
| | | | 204/424 |

* cited by examiner

GAS SENSOR

The present application claims priority from Japanese Patent Application No. 2022-169878, filed on Oct. 24, 2022, the entire contents of which are incorporated herein by reference.

BACKGROUND OF THE INVENTION

1. Field of the Invention

The present invention relates to a gas sensor.

2. Description of the Related Art

Hitherto, a gas sensor that detects the concentration of a specific gas, such as NOx, in a measurement-object gas, such as an exhaust gas of an automobile, is known. For example, PTL 1 describes a gas sensor comprising a sensor element including: an element body that includes an oxygen-ion-conductive solid electrolyte layer, and is internally provided with a measurement-object gas flow portion that introduces a measurement-object gas and causes the measurement-object gas to flow therethrough; an adjustment pump cell that adjusts the oxygen concentration in an oxygen concentration adjustment chamber of the measurement-object gas flow portion; a measurement pump cell having a measurement electrode disposed in a measurement chamber provided downstream of the oxygen concentration adjustment chamber of the measurement-object gas flow portion; and a reference electrode. When the concentration of NOx is detected by the gas sensor, the oxygen concentration in the oxygen concentration adjustment chamber is first adjusted by the adjustment pump cell, and the measurement-object gas with the oxygen concentration adjusted reaches the measurement chamber. In the measurement chamber, the NOx in the measurement-object gas is reduced in the vicinity of the measurement electrode. Then, the oxygen in the vicinity of the measurement electrode is pumped out by performing feedback control on the measurement pump cell so that voltage V2 generated across the measurement electrode and the reference electrode reaches a predetermined target value. The concentration of NOx in the measurement-object gas is detected based on pump current Ip2 which flows then.

It is known that for controlling the element temperature of the gas sensor by a heater, the resistance values of cells are measured. For example, PTL 2 states that a resistance value between two lead wires of an oxygen concentration measurement cell is measured, and an energized state of a heater pattern is controlled so that the measured resistance value is 80Ω corresponding to an element temperature of 740° C.

CITATION LIST

Patent Literature

PTL 1: JP 2022-091669 A
PTL 2: JP 3340110 B

SUMMARY OF THE INVENTION

In the case where the sensor element of the gas sensor includes at least two pump cells, when the heater is controlled based on the impedance measured for one of the pump cells, the temperature of the other pump cell also changes, and the impedance changes. For this reason, the impedance of each of the two pump cells may be uncontrollable at a target value. Thus, due to a change in the impedance of the other pump cell, the accuracy of process performed based on the other pump cell, for example, the accuracy of control of the gas sensor or the accuracy of detection of the specific gas concentration may be reduced. In the gas sensor of PTL 2, when the heater is controlled based on the resistance value of the oxygen concentration measurement cell, the temperature of the other cell and change of the impedance are not taken into consideration.

The present invention has been devised to solve such a problem, and it is a main object to perform both a process using the first pump cell and a process using the second pump cell with high accuracy.

The present invention employs the following device to achieve the above-described main object.

[1] The gas sensor of the present invention is a gas sensor that detects a specific gas concentration which is a concentration of a specific gas in a measurement-object gas, the gas sensor comprising: an element body which includes an oxygen-ion-conductive solid electrolyte layer, and is internally provided with a measurement-object gas flow portion that introduces the measurement-object gas and causes the measurement-object gas to flow; a first pump cell including a first inner electrode disposed in the measurement-object gas flow portion, the first pump cell being configured to perform pumping of oxygen; a second pump cell including a second inner electrode disposed in the measurement-object gas flow portion, the second pump cell being configured to perform pumping of oxygen; a heater configured to heat the element body; a first impedance measurer configured to measure a first impedance by applying a voltage to the first inner electrode; a second impedance measurer configured to measure a second impedance by applying a voltage to the second inner electrode; and a control apparatus configured to perform a heater control process of controlling the heater so that the first impedance reaches a target value, and a correction process of correcting, based on the second impedance, a second pump current which flows through the second pump cell or a value derived based on the second pump current.

In this gas sensor, a first impedance is measured for the first pump cell, and the heater is controlled so that the first impedance reaches a target value, thus the first impedance can be maintained near the target value for the first pump cell. Therefore, any process using the first pump cell can be performed with high accuracy. Meanwhile, even if such a heater control process is performed, the second impedance of the second pump cell does not necessarily reach a desired value. However, in this gas sensor, a second impedance is measured for the second pump cell, and a correction process based on the second impedance is performed. For this reason, a process performed using the second pump cell, particularly, a process based on the second pump current can be performed with high accuracy. Based upon the foregoing, in the gas sensor, both a process using the first pump cell and a process using the second pump cell can be performed with high accuracy. Here, "pumping of oxygen is performed" includes a case where oxygen is pumped out from the measurement-object gas flow portion, and a case where oxygen is pumped into the measurement-object gas flow portion. It is sufficient that each of the first pump cell and the second pump cell be a cell that performs at least one of such pumping-in of oxygen or pumping-out of oxygen.

In this case, the first pump cell may be constituted by including the first inner electrode, a first outer electrode disposed in an area exposed to the measurement-object gas outside the element body, and a solid electrolyte serving as a current path between the first inner electrode and the first outer electrode of the element body. In addition, the second pump cell may be constituted by including the second inner electrode, a second outer electrode disposed in an area exposed to the measurement-object gas outside the element body, and a solid electrolyte serving as a current path between the second inner electrode and the second outer electrode of the element body.

[2] The above-described gas sensor (the gas sensor according to [1]), may further comprise: a reference electrode disposed inside the element body to come into contact with a reference gas which serves as a reference for detecting the specific gas concentration; and an adjustment pump cell including the first pump cell, the adjustment pump cell being configured to adjust an oxygen concentration in an oxygen concentration adjustment chamber of the measurement-object gas flow portion. The first inner electrode may be disposed in the oxygen concentration adjustment chamber, the second inner electrode may be an inner measurement electrode disposed in a measurement chamber provided downstream of the oxygen concentration adjustment chamber of the measurement-object gas flow portion, the second pump cell may be a measurement pump cell that pumps out oxygen originating from the specific gas from the measurement chamber, the control apparatus may perform an adjustment pump control process of controlling the adjustment pump cell so that the oxygen concentration in the oxygen concentration adjustment chamber reaches a target concentration, an oxygen concentration detection process of detecting an oxygen concentration in the measurement-object gas based on a first pump current which is caused to flow through the first pump cell by the adjustment pump control process, a measurement pump control process of feedback controlling a control voltage to be applied to the measurement pump cell so that a voltage across the reference electrode and the inner measurement electrode reaches a target value, and a specific gas concentration detection process of detecting the specific gas concentration in the measurement-object gas based on a measurement pump current that is the second pump current caused to flow through the measurement pump cell by the measurement pump control process. In the correction process, the control apparatus may correct, based on the second impedance, the measurement pump current in the specific gas concentration detection process or the specific gas concentration. In this manner, the first impedance of the first pump cell, that is, the adjustment pump cell is controlled to reach a target value, thus the process performed using the first pump cell, that is, the oxygen concentration detection process can be performed with high accuracy. In addition, for the second pump cell, that is, the measurement pump cell, the measurement pump current is corrected or the specific gas concentration is corrected based on the second impedance, thus the process performed using the second pump cell, that is, the specific gas concentration detection process can be performed with high accuracy.

[3] In the above-described gas sensor (the gas sensor according to [2]), the oxygen concentration adjustment chamber may include a first internal cavity in which the first inner electrode is disposed, and a second internal cavity provided downstream of the first internal cavity and upstream of the measurement chamber of the measurement-object gas flow portion, the adjustment pump cell may include a main pump cell which is the first pump cell, and an auxiliary pump cell having an auxiliary pump electrode disposed in the second internal cavity and being configured to perform pumping of oxygen, and the adjustment pump control process may include a main pump control process of controlling the main pump cell to adjust an oxygen concentration in the first internal cavity, and an auxiliary pump control process of controlling the auxiliary pump cell to adjust an oxygen concentration in the second internal cavity.

[4] In the above-described gas sensor (the gas sensor according to any one of [1] to [3]), the first impedance measurer may measure the first impedance by applying the voltage with a frequency of 1 kHz or higher to the first inner electrode, and the second impedance measurer may measure the second impedance by applying the voltage with a frequency of 1 kHz or higher to the second inner electrode. When a voltage with a relatively high frequency of 1 kHz or higher is applied, and the first impedance is measured, the first impedance is unlikely to contain the reaction resistance of the first inner electrode of the first pump cell, thus the resistance value of the solid electrolyte of the first pump cell is likely to appear, the resistance value being highly correlated with the temperature of the first pump cell. Therefore, the accuracy of control of the temperature of the first pump cell by the heater control process is improved. In addition, when a voltage with a relatively high frequency of 1 kHz or higher is applied, and the second impedance is measured, the second impedance is unlikely to contain the reaction resistance of the second inner electrode of the second pump cell, thus the resistance value of the solid electrolyte of the second pump cell is likely to appear, the resistance value being highly correlated with the temperature of the second pump cell. Therefore, in the correction process based on the second impedance, a change in the second pump current due to a temperature change of the second pump cell is easily corrected. In short, the accuracy of correction in the correction process is improved.

DETAILED DESCRIPTION OF THE INVENTION

Figure 1:
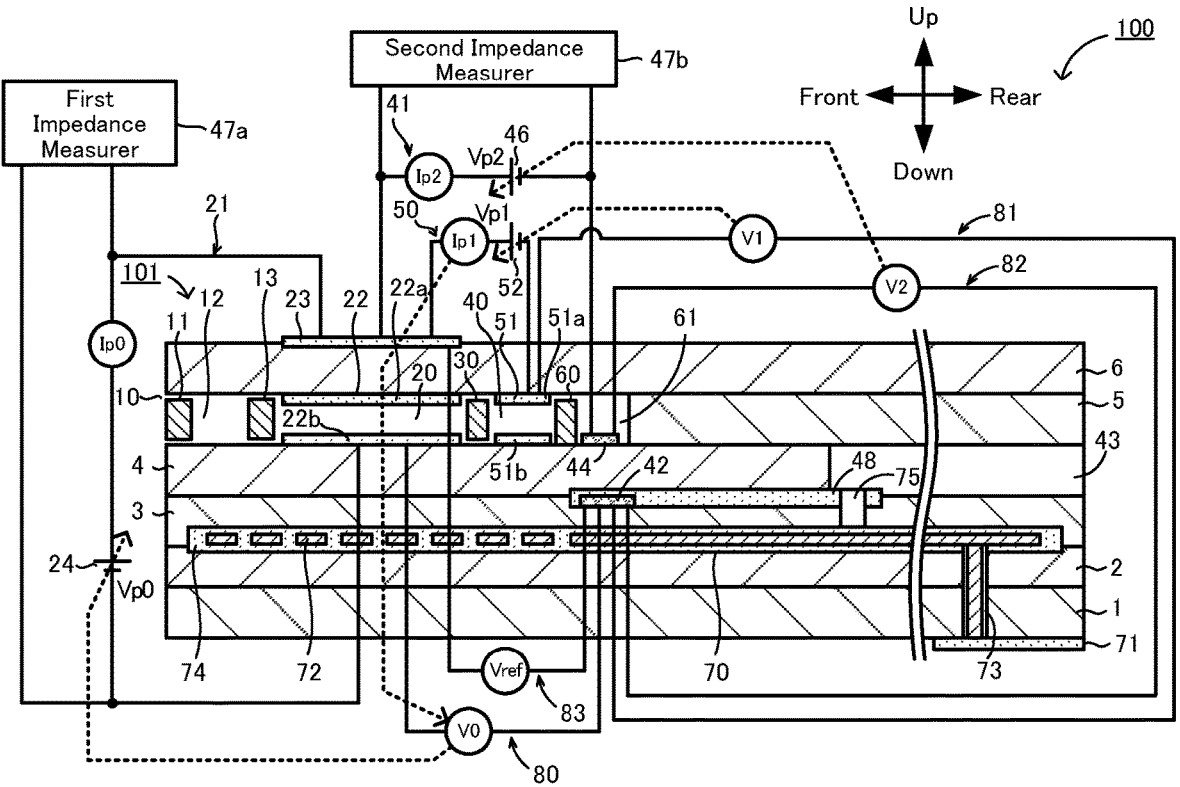
FIG. 1 is a cross-sectional schematic view schematically showing an example of the configuration of a gas sensor 100.
Figure 2:
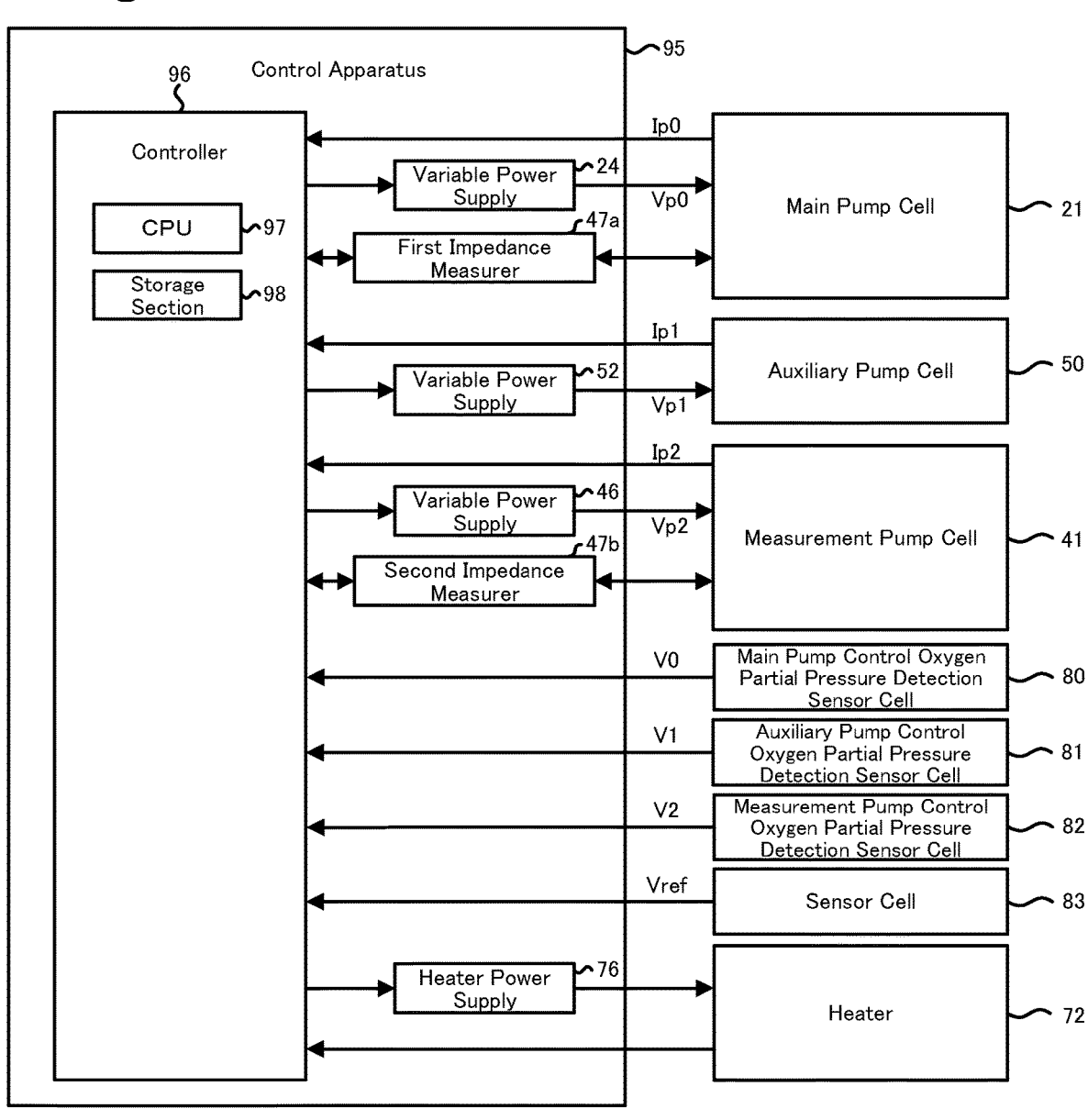
FIG. 2 is a block diagram showing an electrical connection relationship between a control apparatus 95, cells and a heater 72.

Next, an embodiment of the present invention will be described using the drawings. FIG. 1 is a cross-sectional schematic view schematically showing an example of the configuration of a gas sensor 100 that is an embodiment of the present invention. FIG. 2 is a block diagram showing an electrical connection relationship between a control apparatus 95, cells and a heater 72. The gas sensor 100 is, for example, installed in a pipe, such as an exhaust gas pipe of an internal combustion engine. The gas sensor 100 uses the exhaust gas from an internal combustion engine as the measurement-object gas, and detects the concentration of a specific gas, such as NOx and ammonia in the measurement-object gas. In this embodiment, the gas sensor 100 measures the NOx concentration as the specific gas concentration. The gas sensor 100 has a long rectangular parallelepiped sensor element 101, cells 21, 41, 50, 80 to 83 included in the sensor element 101, a heater section 70 provided inside the sensor element 101, and a control apparatus 95 that includes variable power supplies 24, 46, 52 and a heater power supply 76, and controls the entire gas sensor 100.

The sensor element 101 is an element having a layered body in which six layers, that is, a first substrate layer 1, a second substrate layer 2, a third substrate layer 3, a first solid electrolyte layer 4, a spacer layer 5, and a second solid electrolyte layer 6, each made up of an oxygen-ion-conductive solid electrolyte layer made of zirconia ($ZrO_2$) or the like, are laminated in this order from a lower side in the drawing. The solid electrolyte forming these six layers is a dense, airtight one. The sensor element 101 is manufactured by, for example, applying predetermined processing, printing of a circuit pattern, and the like on a ceramic green sheet corresponding to each layer, then laminating those sheets, and further firing the sheets to be integrated.

At a tip end portion side of the sensor element 101 (left end portion side in FIG. 1), a gas inlet port 10, a first diffusion controlled portion 11, a buffer space 12, a second diffusion controlled portion 13, a first internal cavity 20, a third diffusion controlled portion 30, a second internal cavity 40, a fourth diffusion controlled portion 60, and a third internal cavity 61 are formed adjacent to each other so as to communicate with each other in this order between the under surface of the second solid electrolyte layer 6 and the top surface of the first solid electrolyte layer 4.

The gas inlet port 10, the buffer space 12, the first internal cavity 20, the second internal cavity 40, and the third internal cavity 61 are spaces of which top parts, bottom parts, and side parts, provided by hollowing the spacer layer 5, are respectively defined by the under surface of the second solid electrolyte layer 6, the top surface of the first solid electrolyte layer 4, and the side surface of the spacer layer 5 inside the sensor element 101.

Each of the first diffusion controlled portion 11, the second diffusion controlled portion 13, and the third diffusion controlled portion 30 is provided as two laterally long slits (openings of which the longitudinal direction is a direction perpendicular to the drawing). The fourth diffusion controlled portion 60 is provided as a single laterally long slit (an opening of which the longitudinal direction is a direction perpendicular to the drawing) formed as a clearance from the under surface of the second solid electrolyte layer 6. A part from the gas inlet port 10 to the third internal cavity 61 is also referred to as measurement-object gas flow portion.

At a location farther from the tip end side than the measurement-object gas flow portion, a reference gas inlet space 43 is provided between the top surface of the third substrate layer 3 and the under surface of the spacer layer 5 at a location at which the side part is defined by the side surface of the first solid electrolyte layer 4. For example, the atmosphere is introduced into the reference gas inlet space 43 as a reference gas at the time of measuring a NOx concentration.

A reference-gas introduction layer 48 is a layer made of porous ceramics. The reference gas is introduced into the reference-gas introduction layer 48 through the reference gas inlet space 43. The reference-gas introduction layer 48 is formed so as to coat the reference electrode 42.

The reference electrode 42 is an electrode formed in such a manner in which the reference electrode 42 is sandwiched by the top surface of the third substrate layer 3 and the first solid electrolyte layer 4. As described above, the reference-gas introduction layer 48 that communicates with the reference gas inlet space 43 is provided around the reference electrode 42. As will be described later, it is possible to measure an oxygen concentration (oxygen partial pressure) in the first internal cavity 20, an oxygen concentration (oxygen partial pressure) in the second internal cavity 40, and an oxygen concentration (oxygen partial pressure) in the third internal cavity 61 by using the reference electrode 42. The reference electrode 42 is formed as a porous cermet electrode (for example, a cermet electrode of Pt and $ZrO_2$).

In the measurement-object gas flow portion, the gas inlet port 10 is a portion that is open to an external space, and a measurement-object gas is taken into the sensor element 101 from the external space through the gas inlet port 10. The first diffusion controlled portion 11 is a portion that applies predetermined diffusion resistance to a measurement-object gas taken in through the gas inlet port 10. The buffer space 12 is a space provided to guide the measurement-object gas introduced from the first diffusion controlled portion 11 to the second diffusion controlled portion 13. The second diffusion controlled portion 13 is a portion that applies predetermined diffusion resistance to the measurement-object gas introduced from the buffer space 12 into the first internal cavity 20. When the measurement-object gas is introduced from the outside of the sensor element 101 into the first internal cavity 20, the measurement-object gas rapidly taken into the sensor element 101 through the gas inlet port 10 due to pressure fluctuations of the measurement-object gas in the external space (due to pulsation of exhaust pressure when the measurement-object gas is the exhaust gas of an automobile) is not directly introduced into the first internal cavity 20 but, after pressure fluctuations of the measurement-object gas are cancelled out through the first diffusion controlled portion 11, the buffer space 12, and the second diffusion controlled portion 13, the measurement-object gas is introduced into the first internal cavity 20. With this configuration, pressure fluctuations of the measurement-object gas introduced into the first internal cavity 20 are almost ignorable. The first internal cavity 20 is provided as a space used to adjust an oxygen partial pressure in the measurement-object gas introduced through the second diffusion controlled portion 13. The oxygen partial pressure is adjusted by the operation of a main pump cell 21.

The main pump cell 21 is an electrochemical pump cell made up of an inner side pump electrode 22 having a ceiling electrode portion 22a provided substantially all over the under surface of the second solid electrolyte layer 6, facing the first internal cavity 20, an outer pump electrode 23 provided in an area of the top surface of the second solid electrolyte layer 6 so as to be exposed to an external space, the area corresponding to the ceiling electrode portion 22a, the second solid electrolyte layer 6 serving as a current path between these electrodes, the spacer layer 5, and the first solid electrolyte layer 4. The inner pump electrode 22 is formed over the upper and lower solid electrolyte layers (the second solid electrolyte layer 6 and the first solid electrolyte layer 4) defining the first internal cavity 20, and the spacer layer 5 providing a side wall. Specifically, the ceiling electrode portion 22a is formed on the under surface of the second solid electrolyte layer 6, providing a ceiling surface of the first internal cavity 20, a bottom electrode portion 22b is formed on the top surface of the first solid electrolyte layer 4, providing a bottom surface, a side electrode portion (not shown) is formed on the side wall surface (inner surface) of the spacer layer 5, making both side wall portions of the first internal cavity 20, so as to connect those ceiling electrode portion 22a and the bottom electrode portion 22b, and the inner pump electrode 22 is disposed with a structure in a tunnel form at a portion where the side electrode portion is disposed.

The inner pump electrode 22 and the outer pump electrode 23 each are formed as a porous cermet electrode (for example, a cermet electrode of Pt and $ZrO_2$, having an Au content of 1 percent). The inner pump electrode 22 that contacts with a measurement-object gas is formed by using a material of which the reduction ability for NOx components in the measurement-object gas is lowered.

By passing a pump current Ip0 in a positive direction or a negative direction between the inner pump electrode 22 and the outer pump electrode 23 by applying a desired voltage Vp0 between the inner pump electrode 22 and the outer pump electrode 23, the main pump cell 21 is capable of pumping out oxygen in the first internal cavity 20 to the external space or pumping oxygen in the external space into the first internal cavity 20.

In order to detect an oxygen concentration (oxygen partial pressure) in an atmosphere in the first internal cavity 20, an electrochemical sensor cell, that is, a main pump control oxygen partial pressure detection sensor cell 80, is made up of the inner pump electrode 22, the second solid electrolyte layer 6, the spacer layer 5, the first solid electrolyte layer 4, the third substrate layer 3, and the reference electrode 42.

An oxygen concentration (oxygen partial pressure) in the first internal cavity 20 is found by measuring an electromotive force (voltage V0) in the main pump control oxygen partial pressure detection sensor cell 80. In addition, the pump current Ip0 is controlled by executing feedback control over the voltage Vp0 of a variable power supply 24 such that the voltage V0 becomes a target value. With this configuration, it is possible to maintain the oxygen concentration in the first internal cavity 20 at a predetermined constant value.

The third diffusion controlled portion 30 is a portion that applies predetermined diffusion resistance to a measurement-object gas of which the oxygen concentration (oxygen partial pressure) is controlled by operation of the main pump cell 21 in the first internal cavity 20 to guide the measurement-object gas to the second internal cavity 40.

The second internal cavity 40 is provided as a space used to further adjust the oxygen partial pressure by using an auxiliary pump cell 50 for the measurement-object gas adjusted in the oxygen concentration (oxygen partial pressure) in the first internal cavity 20 in advance and then introduced through the third diffusion controlled portion 30. With this configuration, it is possible to highly accurately maintain the oxygen concentration in the second internal cavity 40 at a constant value, so it is possible to measure a highly accurate NOx concentration with the gas sensor 100.

The auxiliary pump cell 50 is an auxiliary electrochemical pump cell made up of an auxiliary pump electrode 51 having a ceiling electrode portion 51a provided substantially all over the under surface of the second solid electrolyte layer 6, facing the second internal cavity 40, the outer pump electrode 23 (not limited to the outer pump electrode 23, and an adequate electrode outside the sensor element 101 may be used), the second solid electrolyte layer 6, the spacer layer 5, and the first solid electrolyte layer 4.

The auxiliary pump electrode 51 is disposed in the second internal cavity 40 with a structure in a similar tunnel form to that of the inner pump electrode 22 provided in the above-described first internal cavity 20. In other words, the auxiliary pump electrode 51 has such a structure in a tunnel form that a ceiling electrode portion 51a is formed on the second solid electrolyte layer 6 providing the ceiling surface of the second internal cavity 40, a bottom electrode portion 51b is formed on the first solid electrolyte layer 4 providing the bottom surface of the second internal cavity 40, a side electrode portion (not shown) that couples those ceiling electrode portion 51a and bottom electrode portion 51b is formed on each of both wall surfaces of the spacer layer 5, providing a side wall of the second internal cavity 40. The auxiliary pump electrode 51, as well as the inner pump electrode 22, is formed by using a material of which the reduction ability for NOx components in the measurement-object gas is lowered.

By applying a desired voltage Vp1 between the auxiliary pump electrode 51 and the outer pump electrode 23, the auxiliary pump cell 50 is capable of pumping out oxygen in an atmosphere in the second internal cavity 40 to the external space or pumping oxygen from the external space into the second internal cavity 40.

In order to control an oxygen partial pressure in an atmosphere in the second internal cavity 40, an electrochemical sensor cell, that is, an auxiliary pump control oxygen partial pressure detection sensor cell 81, is made up of the auxiliary pump electrode 51, the reference electrode 42, the second solid electrolyte layer 6, the spacer layer 5, the first solid electrolyte layer 4, and the third substrate layer 3.

The auxiliary pump cell 50 performs pumping with a variable power supply 52 of which the voltage is controlled in accordance with an electromotive force (voltage V1) detected by the auxiliary pump control oxygen partial pressure detection sensor cell 81. With this configuration, the oxygen partial pressure in an atmosphere in the second internal cavity 40 is controlled to a low partial pressure that substantially does not influence measurement of NOx.

Together with this, its pump current Ip1 is used to control the electromotive force of the main pump control oxygen partial pressure detection sensor cell 80. Specifically, the pump current Ip1 is input to the main pump control oxygen partial pressure detection sensor cell 80 as a control signal, and the gradient of the oxygen partial pressure in the measurement-object gas to be introduced from the third diffusion controlled portion 30 into the second internal cavity 40 is controlled to be constantly unchanged by controlling the above-described target value of the voltage V0. When used as a NOx sensor, the oxygen concentration in the second internal cavity 40 is maintained at a constant value of about 0.001 ppm by the functions of the main pump cell 21 and auxiliary pump cell 50.

The fourth diffusion controlled portion 60 is a portion that applies predetermined diffusion resistance to measurement-object gas of which the oxygen concentration (oxygen partial pressure) is controlled by operation of the auxiliary pump cell 50 in the second internal cavity 40 to guide the measurement-object gas to the third internal cavity 61. The fourth diffusion controlled portion 60 plays a role in limiting the amount of NOx flowing into the third internal cavity 61.

The third internal cavity 61 is provided as a space used to perform a process related to measurement of a nitrogen oxide (NOx) concentration in a measurement-object gas on the measurement-object gas adjusted in oxygen concentration (oxygen partial pressure) in the second internal cavity 40 in advance and then introduced through the fourth diffusion controlled portion 60. Measurement of a NOx concentration is mainly performed by operation of a measurement pump cell 41 in the third internal cavity 61.

The measurement pump cell 41 measures a NOx concentration in the measurement-object gas in the third internal cavity 61. The measurement pump cell 41 is an electrochemical pump cell made up of a measurement electrode 44 provided on the top surface of the first solid electrolyte layer 4, facing the third internal cavity 61, the outer pump electrode 23, the second solid electrolyte layer 6, the spacer layer 5, and the first solid electrolyte layer 4. The measurement electrode 44 is a porous cermet electrode made of a material of which the reduction ability for NOx components in the measurement-object gas is raised as compared to the inner pump electrode 22. The measurement electrode 44 also functions as a NOx reduction catalyst that reduces NOx present in an atmosphere in the third internal cavity 61.

The measurement pump cell 41 is capable of pumping out oxygen produced as a result of decomposition of nitrogen oxides in an atmosphere around the measurement electrode 44 and detecting the amount of oxygen produced as a pump current Ip2.

In order to detect an oxygen partial pressure around the measurement electrode 44, an electrochemical sensor cell, that is, a measurement pump control oxygen partial pressure detection sensor cell 82, is made up of the first solid electrolyte layer 4, the third substrate layer 3, the measurement electrode 44, and the reference electrode 42. A variable power supply 46 is controlled in accordance with an electromotive force (voltage V2) detected by the measurement pump control oxygen partial pressure detection sensor cell 82.

A measurement-object gas guided into the second internal cavity 40 reaches the measurement electrode 44 in the third internal cavity 61 through the fourth diffusion controlled portion 60 in a situation in which the oxygen partial pressure is controlled. Nitrogen oxides in the measurement-object gas around the measurement electrode 44 are reduced ($2NO{\rightarrow}N_2{+}O_2$) to produce oxygen. The produced oxygen is to be pumped by the measurement pump cell 41. At this time, the voltage Vp2 of the variable power supply 46 is controlled such that the voltage V2 detected by the measurement pump control oxygen partial pressure detection sensor cell 82 is constant (target value). The amount of oxygen produced around the measurement electrode 44 is proportional to the concentration of nitrogen oxides in the measurement-object gas, so a nitrogen oxide concentration in the measurement-object gas is calculated by using the pump current Ip2 in the measurement pump cell 41.

When an oxygen partial pressure detection device is constructed as an electrochemical sensor cell by combining the measurement electrode 44, the first solid electrolyte layer 4, the third substrate layer 3, and the reference electrode 42, an electromotive force according to the difference between the amount of oxygen produced by reduction of the NOx component in the atmosphere around the measurement electrode 44, and the amount of oxygen contained in the reference atmosphere can be detected, and accordingly, the concentration of the NOx component in the measurement-object gas can be determined.

An electrochemical sensor cell 83 is made up of the second solid electrolyte layer 6, the spacer layer 5, the first solid electrolyte layer 4, the third substrate layer 3, the outer pump electrode 23, and the reference electrode 42, and it is possible to detect an oxygen partial pressure in a measurement-object gas outside the sensor by using an electromotive force (voltage Vref) obtained by the sensor cell 83.

In the gas sensor 100 having such a configuration, a measurement-object gas of which the oxygen partial pressure is maintained at a constantly unchanged low value (a value that substantially does not influence measurement of NOx) is supplied to the measurement pump cell 41 by operating the main pump cell 21 and the auxiliary pump cell 50. Therefore, it is possible to find a NOx concentration in the measurement-object gas in accordance with a pump current Ip2 that flows as a result of pumping out oxygen, produced by reduction of NOx, by the measurement pump cell 41 substantially in proportion to a NOx concentration in the measurement-object gas.

In addition, the sensor element 101 includes the heater portion 70 that plays a role in temperature adjustment for maintaining the temperature of the sensor element 101 by heating in order to increase the oxygen ion conductivity of the solid electrolyte. The heater portion 70 includes a heater connector electrode 71, a heater 72, a through-hole 73, a heater insulating layer 74, and a pressure release hole 75.

The heater connector electrode 71 is an electrode formed in such a manner as to be in contact with the under surface of the first substrate layer 1. Connection of the heater connector electrode 71 to an external power supply allows electric power to be supplied from the outside to the heater portion 70.

The heater 72 is an electric resistor formed in such a manner as to be sandwiched by the second substrate layer 2 and the third substrate layer 3 from upper and lower sides. The heater 72 is connected to the heater connector electrode 71 via the through-hole 73, and is supplied with electric power from a heater power supply 76 (see FIG. 2) through the heater connector electrode 71 to generate heat to increase and maintain the temperature of the solid electrolyte forming the sensor element 101.

The heater 72 is embedded all over the region from the first internal cavity 20 to the third internal cavity 61, and is capable of adjusting the overall sensor element 101 to a temperature at which the solid electrolyte is activated.

The heater insulating layer 74 is an electrically insulating layer formed of an insulating material, such as alumina, on the top and under surfaces of the heater 72. The heater insulating layer 74 is formed for the purpose of obtaining an electrical insulation property between the second substrate layer 2 and the heater 72 and an electrical insulation property between the third substrate layer 3 and the heater 72.

The pressure release hole 75 is a portion provided so as to extend through the third substrate layer 3 and the reference-gas introduction layer 48 and communicate with the reference gas inlet space 43. The pressure release hole 75 is formed for the purpose of easing an increase in internal pressure resulting from an increase in temperature in the heater insulating layer 74.

As shown in FIG. 2, the control apparatus 95 includes the above-mentioned variable power supplies 24, 46, 52, a first impedance measurer 47a, a second impedance measurer 47b, the above-mentioned heater power supply 76, and a controller 96.

The first impedance measurer 47a is a device that measures a first impedance R1 by applying a voltage to the inner pump electrode 22 (an example of the first inner electrode). The first impedance measurer 47a measures the first impedance R1 by applying a voltage with a predetermined first frequency across the inner pump electrode 22 and the outer pump electrode 23 which are two electrodes included in the main pump cell 21 (an example of the first pump cell). The second impedance measurer 47b is a device that measures a second impedance R2 by applying a voltage to the measurement electrode 44 (an example of the second inner electrode). The second impedance measurer 47b measures the second impedance R2 by applying a voltage with a predetermined second frequency across the measurement electrode 44 and the outer pump electrode 23 which are two electrodes included in the measurement pump cell 41 (an example of the second pump cell). The first impedance measurer 47a and the second impedance measurer 47b each include, for example, a power supply, a voltage measurer and a current measurer which are not illustrated, and measure the first impedance R1 and the second impedance R2 based on the voltage and the current measured by the voltage measurer and the current measurer when a voltage is applied from the power supply.

Figure 3:
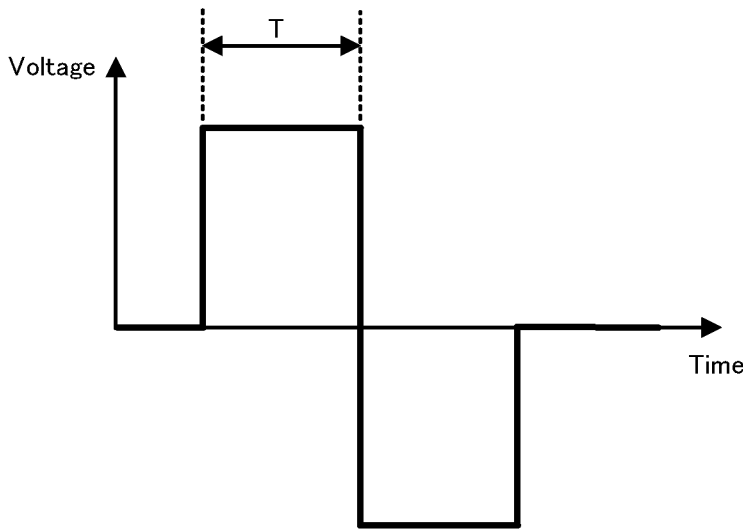
FIG. 3 is a graph showing an example of a pulse voltage applied by first, second impedance measurers 47*a*, 47*b*.

In this embodiment, the first impedance measurer 47a applies a pulse voltage with a square wave shown in FIG. 3 across the inner pump electrode 22 and the outer pump electrode 23 of the main pump cell 21, and measures the amount of change $\Delta V$ in the voltage across the inner pump electrode 22 and the outer pump electrode 23 and the amount of change $\Delta I$ in the current flowing through the main pump cell 21 then. The first impedance measurer 47a then calculates the first impedance R1[$\Omega$] (R1=$\Delta V$/$\Delta I$) by dividing the amount of change $\Delta V$ in voltage by the amount of change $\Delta I$ in current. Similarly, the second impedance measurer 47b applies the pulse voltage shown in FIG. 3 to the measurement pump cell 41, and calculates the second impedance R2[$\Omega$] by dividing the amount of change $\Delta V$ in the voltage across the measurement electrode 44 and the outer pump electrode 23 by the amount of change $\Delta I$ in the current flowing through the measurement pump cell 41.

The first frequency that is the frequency of the voltage applied by the first impedance measurer 47a is preferably 1 kHz or higher. When a voltage with a relatively high frequency of 1 kHz or higher is applied, and the first impedance R1 is measured, the first impedance R1 is unlikely to contain the reaction resistance of the inner pump electrode 22 of the main pump cell 21, thus the resistance value of the solid electrolyte (the layers 4 to 6 in this case) of the main pump cell 21 is likely to appear as the first impedance R1, the resistance value being highly correlated with the temperature of the main pump cell 21. Similarly, the second frequency that is the frequency of the voltage applied by the second impedance measurer 47b is preferably 1 kHz or higher. When a voltage with a relatively high frequency of 1 kHz or higher is applied, and the second impedance R2 is measured, the second impedance R2 is unlikely to contain the reaction resistance of the measurement electrode 44 of the measurement pump cell 41, thus the resistance value of the solid electrolyte (the layers 4 to 6 in this case) of the measurement pump cell 41 is likely to appear as the second impedance R2, the resistance value being highly correlated with the temperature of the measurement pump cell 41. The first frequency and the second frequency each may be 100 kHz or lower. The first frequency and the second frequency may have same value or different values. When the applied voltage is the pulse voltage as in FIG. 3, the frequency of the pulse voltage has the value calculated as $1/(2 \times T)$ [Hz], where T [sec] is the positive-side pulse width of the applied pulse voltage.

The controller 96 is a microprocessor including a CPU 97 and a storage section 98. The storage section 98 is a non-volatile memory capable of rewriting information, and can store various programs and various data, for example. The controller 96 receives input of voltage V0 detected by the main pump control oxygen partial pressure detection sensor cell 80, voltage V1 detected by the auxiliary pump control oxygen partial pressure detection sensor cell 81, voltage V2 detected by the measurement pump control oxygen partial pressure detection sensor cell 82, voltage Vref detected by the sensor cell 83, pump current Ip0 detected by the main pump cell 21, pump current Ip1 detected by the auxiliary pump cell 50 and pump current Ip2 detected by the measurement pump cell 41. The controller 96 controls the voltages Vp0, Vp1, Vp2 output by the variable power supplies 24, 46, 52 by outputting a control signal to the variable power supplies 24, 46, 52, thereby controlling the main pump cell 21, the measurement pump cell 41 and the auxiliary pump cell 50. The controller 96 causes the first, second impedance measurers 47a, 47b to perform impedance measurement by outputting a control signal to the first, second impedance measurers 47a, 47b, and receives input of the values of the first, second impedance R1, R2 from the first, second impedance measurers 47a, 47b as a result of the measurement. The controller 96 controls the electric power to be supplied to the heater 72 by the heater power supply 76 by outputting a control signal to the heater power supply 76. The storage section 98 also stores the later-described target values V0*, V1*, V2*, R1*, etc. The CPU 97 of the controller 96 controls the cells 21, 41, 50 and the heater 72 by referring to these target values V0*, V1*, V2*, R1*.

The controller 96 executes an auxiliary pump control process of controlling the auxiliary pump cell 50 so that the oxygen concentration in the second internal cavity 40 reaches a target concentration. Specifically, the controller 96 controls the auxiliary pump cell 50 by executing feedback control on the voltage Vp1 of the variable power supply 52 so that the voltage V1 reaches a constant value (referred to as target value V1*). The target value V1* is defined as the value that causes the oxygen concentration in the second internal cavity 40 to reach a predetermined low oxygen concentration that does not substantially affect measurement of NOx.

The controller 96 executes a main pump control process of controlling the main pump cell 21 so that the pump current Ip1 which flows at the time of adjusting the oxygen concentration in the second internal cavity 40 by the auxiliary pump cell 50 through the auxiliary pump control process reaches a target current (referred to as target value Ip1*). Specifically, the controller 96 makes setting (feedback control) of a target value (referred to as target value V0*) of the voltage V0 based on the pump current Ip1 so that the pump electric current Ip1 flowing by the voltage Vp1 reaches a constant target current Ip1*. The controller 96 then executes feedback control on the voltage Vp0 of the variable power supply 24 so that the voltage V0 reaches the target value V0* (in other words, the oxygen concentration in the first internal cavity 20 reaches the target concentration). The gradient of oxygen partial pressure in a measurement-object gas to be introduced from the third diffusion controlled portion 30 into the second internal cavity 40 is made unchanged constantly by the main pump control process. The target value V0* is set to a value which causes the oxygen concentration in the first internal cavity 20 to be higher than 0% and a low oxygen concentration. The pump current Ip0 which flows during the main pump control process varies according to the oxygen concentration in a measurement-object gas (that is, a measurement-object gas in the surroundings of the sensor element 101) flowed into the measurement-object gas flow portion through the gas inlet port 10. Thus, the controller 96 can also detect the oxygen concentration in a measurement-object gas based on the pump current Ip0.

The main pump control process and the auxiliary pump control process described above are also collectively referred as an adjustment pump control process. The first internal cavity 20 and the second internal cavity 40 are also collectively referred as an oxygen concentration adjustment chamber. The main pump cell 21 and the auxiliary pump cell 50 are also collectively referred as an adjustment pump cell. The controller 96 executes the adjustment pump control process, and thereby the adjustment pump cell adjusts the oxygen concentration in the oxygen concentration adjustment chamber.

In addition, the controller 96 performs a measurement pump control process of controlling the measurement pump cell 41 so that the voltage V2 reaches a constant value (referred to as target value V2*) (specifically, so that the oxygen concentration in the third internal cavity 61 reaches a predetermined low concentration). Specifically, the controller 96 controls the measurement pump cell 41 by performing feedback control on the voltage Vp2 of the variable power supply 46 so that the voltage V2 reaches the target value V2*. Oxygen is pumped out from the third internal cavity 61 by the measurement pump control process.

Execution of the normal time measurement pump control process causes oxygen to be pumped out from the third internal cavity 61 so that the oxygen produced due to reduction of NOx in a measurement-object gas in the third internal cavity 61 become substantially zero. The controller 96 obtains a pump current Ip2 as a detected value according to the oxygen produced in the third internal cavity 61 from a specific gas (here, NOx), and calculates the NOx concentration in a measurement-object gas based on the pump current Ip2.

The storage section 98 stores a relational expression (for example, an expression of a linear function or a quadratic function) or a map as a correspondence relationship between the pump current Ip2 and the NOx concentration. Such a relational expression or a map may be predetermined by an experiment.

The controller 96 performs a heater control process of controlling the heater 72 so that the first impedance R1 reaches the target value R1*. Specifically, the controller 96 causes the first impedance measurer 47a to measure the first impedance R1, and performs feedback control on the heater power supply 76 so that the measured value reaches the target value R1*. The target value R1* is determined in advance as the value of the first impedance R1, and stored in the storage section 98, where the first impedance R1 corresponds to, for example, a target temperature (for example, 800° C.) of the solid electrolyte (layers 4 to 6 in this case) required to sufficiently increase the pumping ability of the main pump cell 21. For example, when the measured first impedance R1 is higher than the target value R1* (in other words, when the temperature of the main pump cell 21 is lower than the target temperature), the controller 96 controls the heater power supply 76 so that the temperature of the solid electrolyte is raised by increasing the electric power supplied to the heater 72. When passing an electric current through the heater 72, the heater power supply 76 adjusts the electric power supplied to the heater 72 by changing the value of the voltage applied to the heater 72 based on, for example, a control signal from the controller 96.

When the heater control process as described above is performed, the first impedance R1 of the main pump cell 21 can be controlled at the target value R1*, but accordingly, the temperature of the measurement pump cell 41 also changes. In addition, the temperature of the main pump cell 21 and the measurement pump cell 41 is also changed by the temperature of the measurement-object gas, for example. The main pump cell 21 is unlikely to be affected by the temperature of the measurement-object gas because the temperature of the main pump cell 21 is adjusted by the heater control process; however, the temperature of the measurement pump cell 41 is likely to be affected by the temperature of the measurement-object gas. Thus, the second impedance R2 of the measurement pump cell 41 does not necessarily reach a desired value. Change in the second impedance R2 of the measurement pump cell 41 causes the pump current Ip2 to change also, which may have an effect on the accuracy of detection of the NOx concentration. Thus, the inventors studied the relationship between the second impedance R2 of the measurement pump cell 41 and the pump current Ip2. First, as the measurement-object gas, a model gas containing nitrogen as the base gas, an oxygen concentration of 0%, a water concentration of 3%, and an NO concentration of 0 ppm was prepared. Next, the controller 96 starts the above-described heater control with the sensor element 101 exposed to the model gas, then after the first impedance R1 reaches near the target value R1*, the controller 96 further starts the adjustment pump control process and the measurement pump control process.

Figure 4:
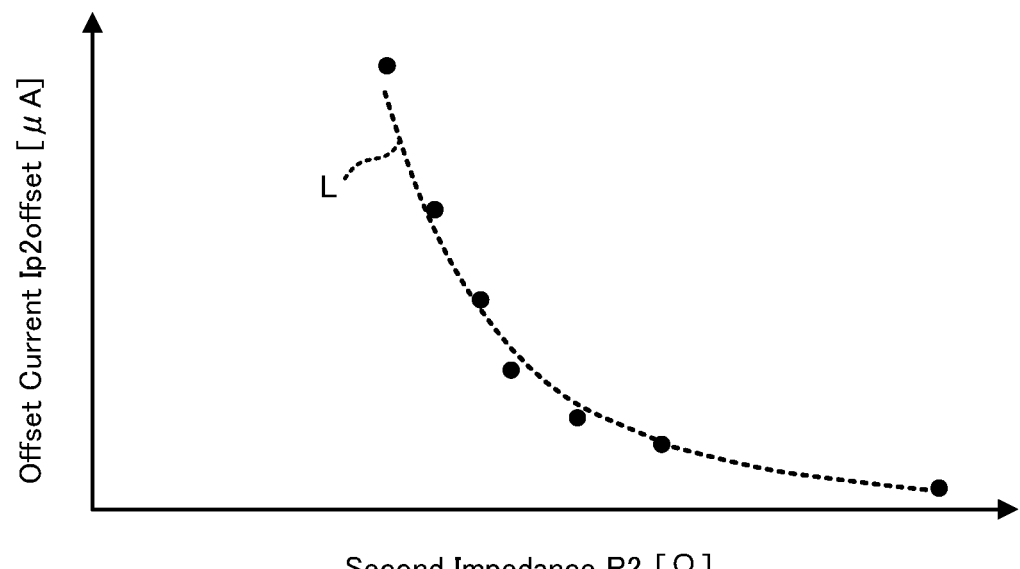
FIG. 4 is a graph showing a relationship between second impedance R2 and offset current Ip2offset.

Subsequently, the value of the pump current Ip2 was measured with the pump current Ip2 stable. Since the model gas has an NO concentration of 0 ppm, the pump current Ip2 is theoretically 0 μA, but actually, a slight pump current Ip2 flows. Such a pump current Ip2 which is caused to flow due to a factor other than the specific gas (NOx in this case) is referred to as an offset current Ip2offset. The offset current Ip2offset is also contained in the pump current Ip2 when the NOx concentration is not 0 ppm. Subsequently, the pump current Ip2 (offset current Ip2offset) was measured by the same method described above except that the second impedance R2 of the measurement pump cell 41 is made different by changing the gas temperature of the model gas. As the relationship between the second impedance R2 and the offset current Ip2offset, the graph shown in FIG. 4 was obtained by these measurements. In FIG. 4, seven points of measurement result are indicated by black dots, and an approximate curve based on the measurement result is indicated by a dashed line as a curve L.

As seen from FIG. 4, it has been identified that the offset current Ip2offset tends to decrease for higher second impedance R2. Like this, there is a correlation between the second impedance R2 and the offset current Ip2offset, thus it is found that the offset current Ip2offset can be derived based on the second impedance R2. Thus, in this embodiment, as the correspondence relationship between the second impedance R2 and the offset current Ip2offset, a relational expression or a map representing the curve L shown in FIG. 4 is pre-stored in the storage section 98. When calculating the NOx concentration in the measurement-object gas, the controller 96 performs the later-described correction process by utilizing the correspondence relationship.

Figure 5:
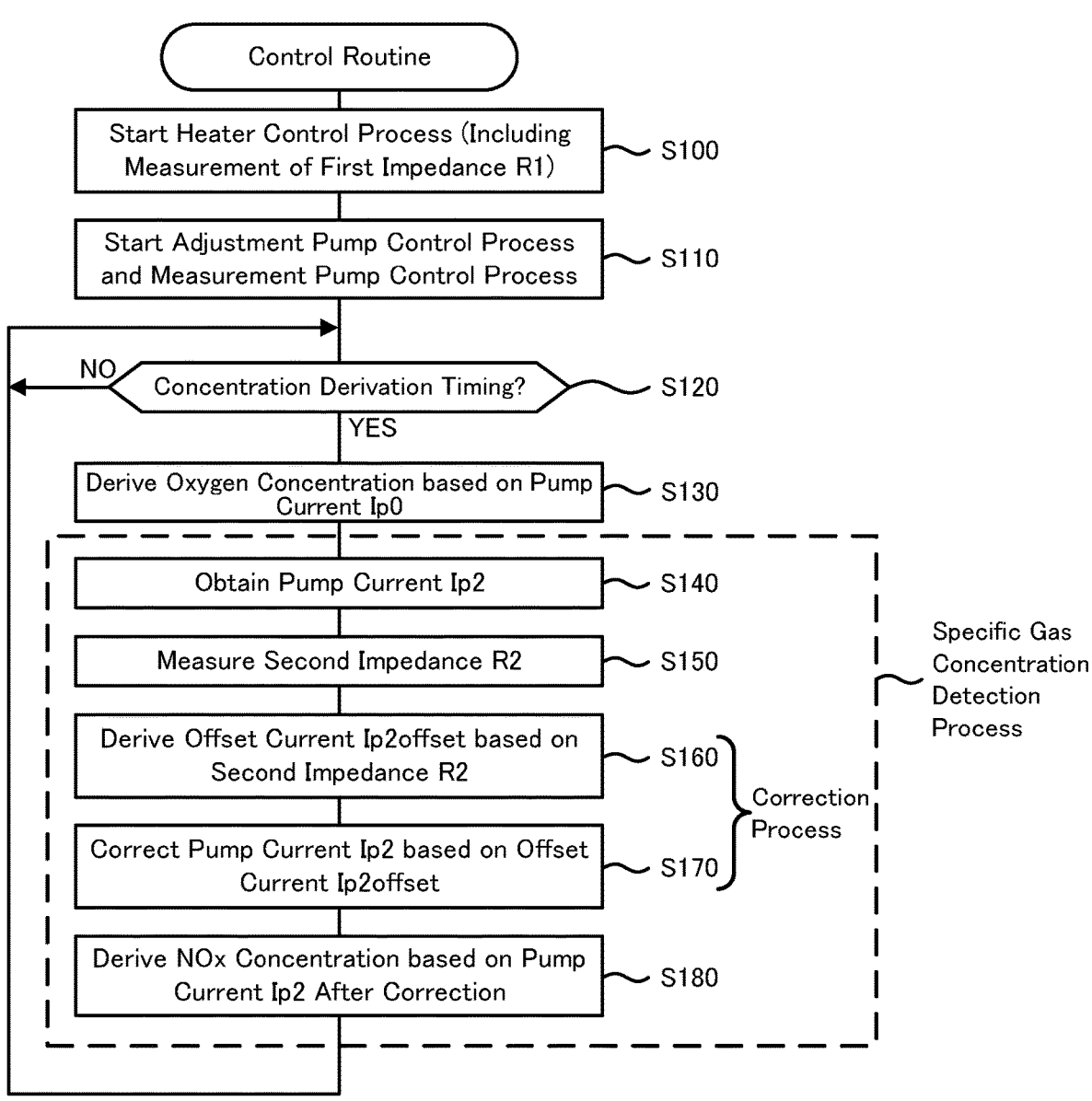
FIG. 5 is a flowchart showing an example of a control routine.

Next, an example of the process of measuring the NOx concentration by the controller 96 of the gas sensor 100 will be described. FIG. 5 is a flowchart showing an example of the control routine executed by the controller 96. The controller 96 stores the routine, for example, in the storage section 98. Upon input of a start command, for example, from an engine ECU which is not illustrated, the controller 96 starts the control routine. Note that in this embodiment, the controller 96 also measures the oxygen concentration in the measurement-object gas.

Upon start of the control routine, the CPU 97 of the controller 96 first starts the above-described heater control process (step S100). When the heater control process is started, the above-described measurement of the first impedance R1 by the first impedance measurer 47a, and the control of the heater 72 by the CPU 97 based on the measured value and the target value R1* are repeatedly performed. Subsequently, the CPU 97 starts the above-described adjustment pump control process and measurement pump control process (step S110). When the first impedance measurer 47a measures the first impedance R1 of the main pump cell 21 after the start of the adjustment pump control process and the measurement pump control process, the CPU 97 preferably controls the variable power supply 24 so that the value of the voltage Vp0 applied to the main pump cell 21 temporarily reduces. In addition, the CPU 97 preferably suspends the main pump control process so that the voltage Vp0 is not applied to the main pump cell 21. In this manner, change in the measurement value of the first impedance R1 due to the effect of the voltage Vp0 can be prevented, and the accuracy of measurement of the first impedance R1 is improved.

Next, the CPU97 determines whether or not a concentration derivation timing for deriving oxygen concentration and NOx concentration has been reached (step S120). For example, at every elapse of a predetermined time or when a concentration derivation command is input from the engine ECU, the CPU 97 determines that a concentration derivation timing has been reached.

When it is determined in step S120 that a concentration derivation timing has been reached, the CPU 97 first performs an oxygen concentration detection process of deriving the oxygen concentration based on the pump current Ip0 (step S130). In the adjustment pump control process (particularly, the main pump control process), the CPU 97 controls the main pump cell 21 so that the voltage V0 reaches the target value V0* (in other words, the oxygen concentration in the first internal cavity 20 reaches the target concentration), thus can derive the oxygen concentration in the measurement-object gas based on the pump current Ip0 as described above. In this embodiment, a relational expression or a map showing the correspondence relationship between the pump current Ip0 and the oxygen concentration is determined by an experiment, and pre-stored in the storage section 98. In step S130, the CPU 97 calculates the oxygen concentration in the measurement-object gas based on the current pump current Ip0 and the correspondence relationship stored in the storage section 98.

Subsequently, the CPU 97 performs a specific gas concentration detection process of detecting the NOx concentration based on the pump current Ip2 (steps S140 to S180). The specific gas concentration detection process includes a correction process (steps S160, S170) of correcting the pump current Ip2 based on the second impedance R2. In the specific gas concentration detection process, the CPU 97 first obtains the pump current Ip2 which is caused to flow by the measurement pump control process (step S140). Next, the CPU 97 causes the second impedance measurer 47b to measure the second impedance R2 of the measurement pump cell 41, and acquires the value obtained (step S150). Either one of step S140 and step S150 may be executed first. In the same manner as at the time of measurement of the first impedance R1, when the second impedance measurer 47b measures the second impedance R2 of the measurement pump cell 41 in step S150, the CPU 97 preferably controls the variable power supply 46 so that the value of the voltage Vp2 applied to the measurement pump cell 41 temporarily reduces. In addition, the CPU 97 preferably suspends the measurement pump control process so that the voltage Vp2 is not applied to the measurement pump cell 41.

Subsequently, the CPU 97 derives the offset current Ip2offset corresponding to the second impedance R2 based on the measured second impedance R2, and the correspondence relationship (e.g., the relationship of the curve L of FIG. 4) between the second impedance R2 and the offset current Ip2offset stored in the storage section 98 (step S160). The CPU 97 then corrects the pump current Ip2 obtained in step S140 based on the derived offset current Ip2offset (step S170). Specifically, the CPU 97 derives the pump current Ip2 after correction by subtracting the offset current Ip2offset derived in step S160 from the pump current Ip2 obtained in step S140. Consequently, the pump current Ip2 after correction has a value with eliminated effect of a change in the offset current Ip2offset due to a change in the second impedance R2. Subsequently, the CPU 97 derives the NOx concentration based on the pump current Ip2 after correction (step S180). Specifically, the CPU 97 derives NOx concentration corresponding to the pump current Ip2 after correction based on the pump current Ip2 after correction, and the correspondence relationship between the pump current Ip2 and the NOx concentration stored in the storage section 98. The NOx concentration derived in this manner has a value which is unlikely to be affected by a change in the offset current Ip2offset due to a change in the second impedance R2, thus the derived NOx concentration has a highly accurate value closer to the actual NOx concentration, as compared to when the pump current Ip2 is not corrected. As described above, in this embodiment, the NOx concentration is derived based on the corrected pump current Ip2 obtained by subtracting the offset current Ip2offset from the pump current Ip2, thus regarding the correspondence relationship between the pump current Ip2 and the NOx concentration to be pre-stored in the storage section 98, it is sufficient that a correspondence relationship between the corrected pump current Ip2 and the NOx concentration be prepared similarly. Alternatively, a correspondence relationship between the pump current Ip2 and the NOx concentration with an offset current Ip2offset of a predetermined reference value may be pre-stored in the storage section 98. In this case, the CPU 97 may derive the difference between the offset current Ip2offset derived in step S160 and the reference value, as a correction amount, and may derive the pump current Ip2 after correction by subtracting the correction amount from the pump current Ip2 obtained in step S140.

After step S180, or when a concentration derivation timing has not been reached in step S120, the CPU 97 executes the processes in and after S120. The CPU 97 repeatedly measures the oxygen concentration and the NOx concentration in the measurement-object gas by executing the control routine as described above.

The correspondence relationships between the components in this embodiment and the components in the present invention will now be clarified. A layered body obtained by layering six layers consisting of the first substrate layer 1, the second substrate layer 2, the third substrate layer 3, the first solid electrolyte layer 4, the spacer layer 5 and the second solid electrolyte layer 6 in that order corresponds to an element body of the present invention, the inner pump electrode 22 corresponds to a first inner electrode, the main pump cell 21 corresponds to a first pump cell, the measurement electrode 44 corresponds to a second inner electrode, the measurement pump cell 41 corresponds to a second pump cell, the heater 72 corresponds to a heater, the first impedance measurer 47a corresponds to a first impedance measurer, the second impedance measurer 47b corresponds to a second impedance measurer, the pump current Ip2 corresponds to a second pump current, and the control apparatus 95 corresponds to a control apparatus. In addition, the outer pump electrode 23 corresponds to a first outer electrode and a second outer electrode, the first internal cavity 20 and the second internal cavity 40 correspond to an oxygen concentration adjustment chamber, the main pump cell 21 and the auxiliary pump cell 50 correspond to an adjustment pump cell, the third internal cavity 61 corresponds to a measurement chamber, the measurement electrode 44 corresponds to an inner measurement electrode, the pump current Ip0 corresponds to a first pump current, and the pump current Ip2 corresponds to a measurement pump current.

With the gas sensor 100 in this embodiment described in detail above, the first impedance R1 is measured for the main pump cell 21, and the heater 72 is controlled so that the first impedance R1 reaches the target value R1*, thus the first impedance R1 can be maintained near the target value R1* for the main pump cell 21. Therefore, any process using the main pump cell 21 can be performed with high accuracy. For example, adjustment of the oxygen concentration in the first internal cavity 20 using the main pump cell 21 can be made with high accuracy. In this embodiment, the oxygen concentration detection process is performed using the pump current Ip0 of the main pump cell 21, thus the oxygen concentration in the measurement-object gas can also be detected with high accuracy. In addition, the second impedance R2 is measured for the measurement pump cell 41, and the correction process based on the second impedance R2 is performed. Thus, any process using the measurement pump cell 41, particularly, the process based on the pump current Ip2 of the measurement pump cell 41 can be performed with high accuracy. For example, in this embodiment, the specific gas concentration detection process of detecting the NOx concentration is performed based on the pump current Ip2, thus the NOx concentration in the measurement-object gas can be detected with high accuracy. Based upon the foregoing, in the gas sensor 100, a process using the main pump cell 21 and a process using the measurement pump cell 41 both can be performed with high accuracy.

Also, the first impedance measurer 47a measures the first impedance R1 by applying a voltage with a frequency of 1 kHz or higher to the inner pump electrode 22, thus the resistance value of the solid electrolyte of the main pump cell 21 is likely to appear in the first impedance R1, the resistance value being highly correlated with the temperature of the main pump cell 21. Thus, the accuracy of control of the temperature of the main pump cell 21 by the heater control process is improved. Furthermore, the second impedance measurer 47b measures the second impedance R2 by applying a voltage with a frequency of 1 kHz or higher to the measurement electrode 44, thus the resistance value of the solid electrolyte of the measurement pump cell 41 is likely to appear in the second impedance R2, the resistance value being highly correlated with the temperature of the measurement pump cell 41. Therefore, in the correction process based on the second impedance R2, a change in the second pump current Ip2 due to a temperature change of the measurement pump cell 41 is easily corrected. In short, the accuracy of correction in the correction process is improved.

Note that the present invention is not limited to the above-described embodiment at all, and may be, of course, implemented in various modes within the technical scope of the present invention.

In the above-described embodiment, the voltage applied by the first, second impedance measurers 47a, 47b is a pulse voltage with a square wave, but is not limited thereto, and may be a periodic voltage. For example, a voltage with a triangular wave or a sine wave may be applied.

In the above-described embodiment, the first impedance measurer 47a applies a voltage across the inner pump electrode 22 and the outer pump electrode 23 which are a pair of electrodes included in the main pump cell 21, but without being limited to this, the first impedance measurer 47a may apply a voltage to at least the inner pump electrode 22 disposed in the measurement-object gas flow portion. For example, the first impedance measurer 47a may measure the first impedance R1 by applying a voltage across the inner pump electrode 22 and the reference electrode 42. Even in this case, the first impedance R1 can be measured as a value including at least the resistance value of the solid electrolyte around the inner pump electrode 22. Similarly, the second impedance measurer 47b may apply a voltage to at least the measurement electrode 44, or may apply a voltage across the measurement electrode 44 and the reference electrode 42, for example.

In the above-described embodiment, the controller 96 corrects the pump current Ip2 based on the second impedance R2, but may correct a value derived based on the pump current Ip2. For example, a correspondence relationship between the second impedance R2 and the correction amount of NOx concentration may be studied in advance, and stored in the storage section 98. In this case, the controller 96 may derive the NOx concentration after correction using the NOx concentration derived based on the obtained pump current Ip2, and a correction amount derived based on the second impedance R2 measured. Alternatively, a correspondence relationship between the pump current Ip2, the second impedance R2 and the NOx concentration may be studied in advance, and stored in the storage section 98. In this case, the controller 96 may derive the NOx concentration based on the obtained pump current Ip2, the second impedance R2 measured, and the correspondence relationship. Thus, derived NOx concentration corresponds to the NOx concentration after correction with the second impedance R2 taken into consideration.

In the above-described embodiment, a case has been described in which the main pump cell 21 is the first pump cell for which the first impedance is to be measured, and the measurement pump cell 41 is the second pump cell for which the second impedance is to be measured, but the configuration is not limited thereto. One of the pump cells included in the sensor element 101 may correspond to the first pump cell (the first pump cell having the first inner electrode disposed in the measurement-object gas flow portion, and being configured to perform pumping of oxygen), and another one may correspond to the second pump cell (the second pump cell having the second inner electrode disposed in the measurement-object gas flow portion, and being configured to perform pumping of oxygen). For example, the sensor element 101 in the above-described embodiment includes three pump cells: the main pump cell 21, the auxiliary pump cell 50, and the measurement pump cell 41, thus one of these may be the first pump cell, and another one may be the second pump cell. For example, instead of the measurement pump cell 41, the auxiliary pump cell 50 may be the second pump cell. In this case, the second impedance measurer 47b may measure the impedance of the auxiliary pump cell 50 as the second impedance R2, and the controller 96 may correct, based on the second impedance R2, the pump current Ip1 or a value based on the pump current Ip1. For example, even with the same composition of the measurement-object gas, during execution of the above-described heater control process, adjustment pump control process, and measurement pump control process, the pump current Ip1 flowing through the auxiliary pump cell 50 may change due to a change in the second impedance R2 of the auxiliary pump cell 50. Specifically, the pump current Ip1 includes the offset current Ip1offset which may be correlated with the second impedance R2. In this case, a correspondence relationship between the second impedance R2 of the auxiliary pump cell 50 and the offset current Ip1offset is pre-stored in the storage section 98. The controller 96 then derives the offset current Ip1offset based on the second impedance R2 of the auxiliary pump cell 50, and derives, as the pump current Ip1 after correction, the value obtained by subtracting the offset current Ip1offset from the pump current Ip1. The controller 96 then performs the main pump control process by setting (feedback-controlling) the target value V0* of the voltage V0 based on the pump current Ip1 after correction so that the pump current Ip1 after correction reaches the target value Ip1*. In this manner, any process using the auxiliary pump cell 50, for example, the main pump control process and the auxiliary pump control process can be performed with high accuracy. Note that the controller 96 may correct the target value V0* derived based on the pump current Ip1 instead of correcting the pump current Ip1.

In the above-described embodiment, the impedance of the main pump cell 21 and the measurement pump cell 41 is measured; however, in addition to this, the impedance (third impedance R3) of the auxiliary pump cell 50 may be further measured, and the pump current Ip1 may be corrected based on the third impedance, or a value derived from the pump current Ip1 based on the third impedance may be corrected. In this manner, when the impedance of each of three or more pump cells included in the sensor element 101 is measured, the measurement of the first impedance and the heater control process described above may be performed for one of the pump cells, and measurement of the impedance and the correction process may be performed for each of the pump cells other than the one pump cell.

Although no description is given in the above-described embodiment, the gas sensor 100 is preferably configured such that temperature Tp>temperature Tq>temperature Tm, where Tp, Tq, Tm be the temperatures of the inner pump electrode 22, the auxiliary pump electrode 51, and the measurement electrode 44, respectively in the gas sensor 100 when the heater 72 is at least heated to a temperature in a temperature range of 700° C. or higher and 900° C. or lower. The amount of oxygen to be pumped out from the measurement-object gas flow portion is the greatest for the main pump cell 21, the second greatest for the auxiliary pump cell 50, and relatively smaller for the first measurement pump cell 41, thus the pumping ability of the main pump cell 21 and the auxiliary pump cell 50 can be sufficiently enhanced by satisfying the aforementioned temperature magnitude relationship. When the temperatures of a plurality of electrodes disposed in the measurement-object gas flow portion are made different like this, as in the above-described embodiment, it is preferable that the first pump cell be the pump cell (the main pump cell 21 in this case) including the electrode (the inner pump electrode 22 in this case) which is desired to be adjusted to a highest temperature. In this manner, the measurement of the first impedance and the heater control process are performed on the pump cell including the electrode which is desired to be adjusted to a highest temperature, thus the temperature can be adjusted to the target temperature.

In the above-described embodiment, the gas sensor 100 separately includes the first impedance measurer 47a and the second impedance measurer 47b; however, one impedance measurer may have both functions of the first impedance measurer 47a and the second impedance measurer 47b. In the above-described embodiment, the functions of the control apparatus 95 may be shared by a plurality of apparatuses. For example, an apparatus that performs the heater control process, and an apparatus that performs the correction process may be separately provided.

In the above-described embodiment, the oxygen concentration adjustment chamber has the first internal cavity 20 and the second internal cavity 40; however, the configuration is not limited thereto, and for example, the oxygen concentration adjustment chamber may further include another internal cavity, or one of the first internal cavity 20 and the second internal cavity 40 may be omitted. Similarly, in the above-described embodiment, the adjustment pump cell has the main pump cell 21 and the auxiliary pump cell 50; however, the configuration is not limited thereto, and for example, the adjustment pump cell may include another pump cell, or one of the main pump cell 21 and the auxiliary pump cell 50 may be omitted. For example, when the oxygen concentration in the measurement-object gas can be sufficiently reduced by the main pump cell 21 only, the auxiliary pump cell 50 may be omitted. When the auxiliary pump cell 50 is omitted, the controller 96 only needs to perform the main pump control process as the adjustment pump control process. In the main pump control process, the above-described setting of the target value V0* based on the pump current Ip1 may be omitted. Specifically, a predetermined target value V0* may be pre-stored in the storage section 98, and the controller 96 may control the main pump cell 21 by performing feedback control on the voltage Vp0 of the variable power supply 24 so that the voltage V0 reaches the target value V0*.

Figure 6:
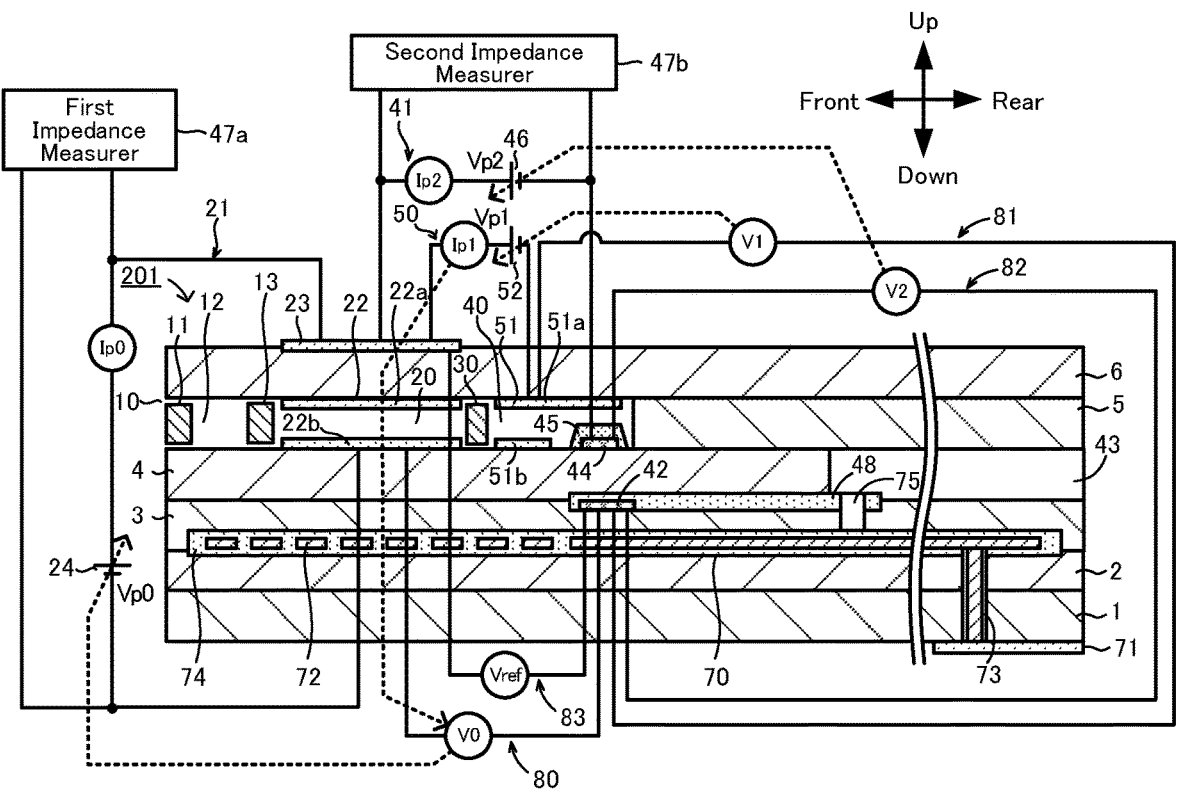
FIG. 6 is a schematic cross-sectional view of a sensor element 201 according to a modification.

In the above-described embodiment, the sensor element 101 of the gas sensor 100 includes the first internal cavity 20, the second internal cavity 40, and the third internal cavity 61; however, the configuration is not limited thereto. For example, as in the sensor element 201 of FIG. 6, the third internal cavity 61 may not be provided. In the sensor element 201 according to the modification shown FIG. 6, the gas inlet 10, the first diffusion control section 11, the buffer space 12, the second diffusion control section 13, the first internal cavity 20, the third diffusion control section 30, and the second internal cavity 40 are formed adjacent to each other so as to communicate with each other in this order between the under surface of the second solid electrolyte layer 6 and the top surface of the first solid electrolyte layer 4. In addition, the measurement electrode 44 is disposed in the top surface of the first solid electrolyte layer 4 in the second internal cavity 40. The measurement electrode 44 is covered by the fourth diffusion control section 45. The fourth diffusion control section 45 is a membrane composed of a ceramic porous body such as alumina ($Al_2O_3$). As with the fourth diffusion control section 60 in the above-described embodiment, the fourth diffusion control section 45 plays a role in limiting the amount of NOx flowing into measurement electrode 44. In addition, the fourth diffusion control section 45 also functions as a protective membrane of the measurement electrode 44. The ceiling electrode portion 51a of the auxiliary pump electrode 51 is formed up to just above the measurement electrode 44. With the thus configured sensor element 201 as well, it is possible to detect a NOx concentration based on, for example, a pump current Ip2 as in the case of the above-described embodiment. In this case, the vicinity of the measurement electrode 44 functions as a measurement chamber.

In the above-described embodiment, the outer pump electrode 23 plays a role as the electrode (also referred to as the outer main pump electrode) to be paired with the inner pump electrode 22, a role as the electrode (also referred to as the outer auxiliary pump electrode) to be paired with the auxiliary pump electrode 51 of the auxiliary pump cell 50, and a role as the electrode (also referred to as the outer measurement electrode) to be paired with the measurement electrode 44 of the measurement pump cell 41 in the main pump cell 21; however, the configuration is not limited thereto. One or more of the outer main pump electrode, the outer auxiliary pump electrode, and the outer measurement electrode may be provided separately from the outer pump electrode 23 outside the element body so as to be in contact with the measurement-object gas.

In the above-described embodiment, the sensor element 101 detects the NOx concentration in the measurement-object gas; however, as long as the sensor element 101 detects the concentration of a specific gas in the measurement-object gas, the configuration is not limited thereto. For example, not only NOx, but also another oxide concentration may serve as the specific gas concentration. When the specific gas is an oxide, as in the above-described embodiment, oxygen is produced when the specific gas itself is reduced in the third internal cavity 61, thus the measurement pump cell 41 can detect the specific gas concentration by obtaining a detection value (e.g., the pump current Ip2) corresponding to the oxygen. Alternatively, the specific gas may be a non-oxide such as ammonia. When the specific gas is a non-oxide, the specific gas is converted to an oxide (for example, ammonia is converted to NO), thereby producing oxygen when the gas after the conversion is reduced in the third internal cavity 61, thus the measurement pump cell 41 can detect the specific gas concentration by obtaining a detection value (e.g., the pump current Ip2) corresponding to the oxygen. For example, the inner pump electrode 22 in the first internal cavity 20 functions as a catalyst, thus ammonia can be converted to NO in the first internal cavity 20.

In the above-described embodiment, the element body of the sensor element 101 is a layered body having a plurality of solid electrolyte layers (layers 1 to 6), but is not limited thereto. The element body of the sensor element 101 may include at least one oxygen-ion-conductive solid electrolyte layer. For example, in FIG. 1, the layers 1 to 5 other than the second solid electrolyte layer 6 may be layers (e.g., layers composed of alumina) composed of a material other than that of solid electrolyte layers. In this case, the electrodes of the sensor element 101 may be disposed in the second solid electrolyte layer 6. For example, the measurement electrode 44 in FIG. 1 may be disposed on the under surface of the second solid electrolyte layer 6. Also, the reference-gas introduction space 43 may be provided in the spacer layer 5 instead of the first solid electrolyte layer 4, the reference-gas introduction layer 48 may be provided between the second solid electrolyte layer 6 and the spacer layer 5 instead of between the first solid electrolyte layer 4 and the third substrate layer 3, and the reference electrode 42 may be provided rearward of the third internal cavity 61 and on the under surface of the second solid electrolyte layer 6.

In the above-described embodiment, the controller 96 sets (feedback-controls) the target value V0* of the voltage V0 based on the pump current Ip1 so that the pump current Ip1 reaches the target value Ip1*, and feedback-controls the pump voltage Vp0 so that the voltage V0 reaches the target value V0*, but may perform another control. For example, the controller 96 may feedback-control the pump voltage Vp0 based on the pump current Ip1 so that the pump current Ip1 reaches the target value Ip1*. In other words, the controller 96 may omit acquisition of the voltage V0 from the main pump control oxygen partial pressure detection sensor cell 80 and setting of the target value V0*, and may directly control the pump voltage Vp0 (eventually, control the pump current Ip0) based on the pump current Ip1.

What is claimed is:

1. A gas sensor that detects a specific gas concentration which is a concentration of a specific gas in a measurement-object gas, the gas sensor comprising:

an element body which includes an oxygen-ion-conductive solid electrolyte layer, and is internally provided with a measurement-object gas flow portion that introduces the measurement-object gas and causes the measurement-object gas to flow;

a first pump cell including a first inner electrode disposed in the measurement-object gas flow portion, the first pump cell being configured to perform pumping of oxygen;

a second pump cell including a second inner electrode disposed in the measurement-object gas flow portion, the second pump cell being configured to perform pumping of oxygen;

a heater configured to heat the element body;

a first impedance measurer configured to measure a first impedance by applying a voltage to the first inner electrode;

a second impedance measurer configured to measure a second impedance by applying a voltage to the second inner electrode;

a control apparatus configured to perform a heater control process of controlling the heater so that the first impedance reaches a target value, and a correction process of correcting, based on the second impedance, a second pump current which flows through the second pump cell or a value derived based on the second pump current;

a reference electrode disposed inside the element body to come into contact with a reference gas which serves as a reference for detecting the specific gas concentration; and an adjustment pump cell including the first pump cell, the adjustment pump cell being configured to adjust an oxygen concentration in an oxygen concentration adjustment chamber of the measurement-object gas flow portion, wherein the first inner electrode is disposed in the oxygen concentration adjustment chamber, the second inner electrode is an inner measurement electrode disposed in a measurement chamber provided downstream of the oxygen concentration adjustment chamber of the measurement-object gas flow portion, the second pump cell is a measurement pump cell that pumps out oxygen originating from the specific gas from the measurement chamber, the control apparatus performs an adjustment pump control process of controlling the adjustment pump cell so that the oxygen concentration in the oxygen concentration adjustment chamber reaches a target concentration, an oxygen concentration detection process of detecting an oxygen concentration in the measurement-object gas based on a first pump current which is caused to flow through the first pump cell by the adjustment pump control process, a measurement pump control process of feedback controlling a control voltage to be applied to the measurement pump cell so that a voltage across the reference electrode and the inner measurement electrode reaches a target value, and a specific gas concentration detection process of detecting the specific gas concentration in the measurement-object gas based on a measurement pump current that is the second pump current caused to flow through the measurement pump cell by the measurement pump control process, and in the correction process, the control apparatus corrects, based on the second impedance, the measurement pump current in the specific gas concentration detection process or the specific gas concentration.

2. The gas sensor according to claim 1, wherein the oxygen concentration adjustment chamber includes a first internal cavity in which the first inner electrode is disposed, and a second internal cavity provided downstream of the first internal cavity and upstream of the measurement chamber of the measurement-object gas flow portion, the adjustment pump cell includes a main pump cell which is the first pump cell, and an auxiliary pump cell having an auxiliary pump electrode disposed in the second internal cavity and being configured to perform pumping of oxygen, and the adjustment pump control process includes a main pump control process of controlling the main pump cell to adjust an oxygen concentration in the first internal cavity, and an auxiliary pump control process of controlling the auxiliary pump cell to adjust an oxygen concentration in the second internal cavity.

3. A gas sensor that detects a specific gas concentration which is a concentration of a specific gas in a measurement-object gas, the gas sensor comprising:

24 an element body which includes an oxygen-ion-conductive solid electrolyte layer, and is internally provided with a measurement-object gas flow portion that introduces the measurement-object gas and causes the measurement-object gas to flow;

a first pump cell including a first inner electrode disposed in the measurement-object gas flow portion, the first pump cell being configured to perform pumping of oxygen;

a second pump cell including a second inner electrode disposed in the measurement-object gas flow portion, the second pump cell being configured to perform pumping of oxygen;

a heater configured to heat the element body;

a first impedance measurer configured to measure a first impedance by applying a voltage to the first inner electrode;

a second impedance measurer configured to measure a second impedance by applying a voltage to the second inner electrode;

a control apparatus configured to perform a heater control process of controlling the heater so that the first impedance reaches a target value, and a correction process of correcting, based on the second impedance, a second pump current which flows through the second pump cell or a value derived based on the second pump current;

wherein the first impedance measurer measures the first impedance by applying the voltage with a frequency of 1 kHz or higher to the first inner electrode, and the second impedance measurer measures the second impedance by applying the voltage with a frequency of 1 kHz or higher to the second inner electrode.

* * * * *